United States Patent [19]

Hirschman

[11] 4,175,561
[45] Nov. 27, 1979

[54] FEMININE HYGIENIC PADS WITH IMPROVED ABSORPTION

[76] Inventor: Shalom Z. Hirschman, 110-11 Queens Blvd., Forest Hills, N.Y. 11375

[21] Appl. No.: 767,586

[22] Filed: Feb. 10, 1977

[51] Int. Cl.² ........................ A61F 13/00; A61F 13/20
[52] U.S. Cl. ..................................... 128/296; 128/285; 28/106; 28/118; 128/270
[58] Field of Search ............... 128/270, 271, 284, 285, 128/287, 290 R, 296

[56] References Cited

U.S. PATENT DOCUMENTS

| D. 247,368 | 2/1978 | Whitehead | 128/290 R |
| D. 247,372 | 2/1978 | Whitehead | 128/290 R |
| 2,499,414 | 3/1950 | Rabell | 128/285 |
| 2,508,214 | 5/1950 | Biederman | 128/285 |
| 3,084,689 | 4/1963 | Moro et al. | 128/270 |
| 3,335,726 | 8/1967 | Maranto | 128/270 |
| 3,499,448 | 3/1970 | Jones | 128/285 |
| 3,726,277 | 4/1973 | Hirschman | 128/285 |
| 3,811,445 | 5/1974 | Dostal | 128/290 R |
| 4,027,672 | 6/1977 | Karami | 128/284 |

FOREIGN PATENT DOCUMENTS

| 1815541 | 7/1970 | Fed. Rep. of Germany | 128/285 |
| 348237 | 9/1960 | Switzerland | 128/290 R |
| 855537 | 12/1960 | United Kingdom | 128/285 |

*Primary Examiner*—Robert W. Michell

[57] ABSTRACT

Feminine Hygienic Pads with improved absorption properties for use in the interlabial space in the area of the female urethral meatus and vaginal meatus for absorbing urine and other undesirable exudations comprising an elongated fibrous pad base of cylindrical, elliptical, polygonal or similar regular shape, the surface of the pad base being formed with multiple flutings, a multiplicity of absorptive cells or pin-cushioning or being formed wholly or in part of shaggy material to increase the absorptive surface area of the pad.

I also provide methods of forming elongated fibrous feminine hygienic pads for interlabial use comprising the steps of applying flutings, absorptive cells or pin-cushioning to either continuous or discontinuous strands of absorptive material travelling in one direction, the flutings or the like being applied by fingers moving back and forth at right angles to the direction of travel of the strand and compacting the fibrous material at the points of contact, the movement of the strand being momentarily arrested as the fingers contact the strand, and cutting off segments.

Short pieces of yarn-like material may be sewn to the pad, or shaggy material as folded into the form of the pad and stitched together. Shaggy material may also be used to cover a base of smooth material so as to provide interlabial pads with surfaces of improved absorptive capacity.

5 Claims, 23 Drawing Figures

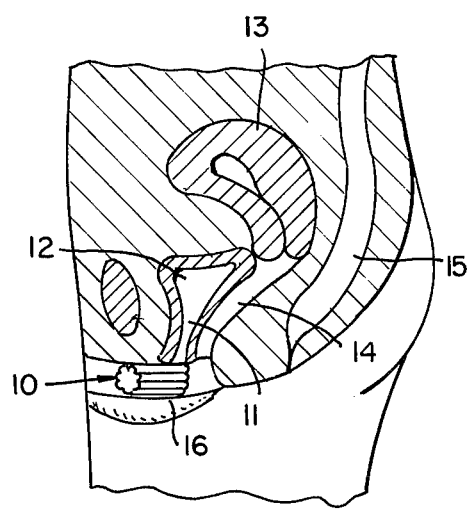
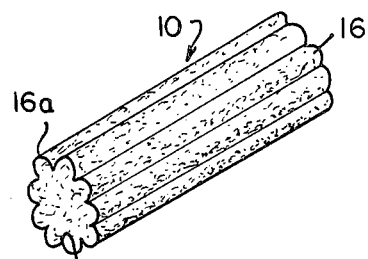
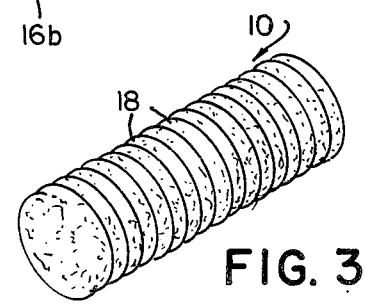
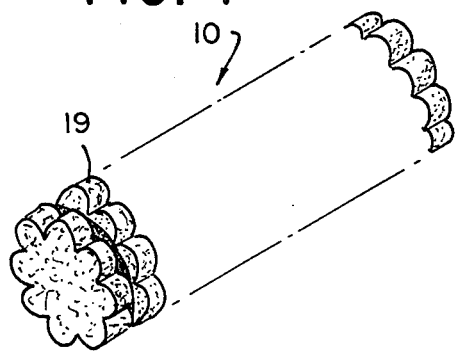
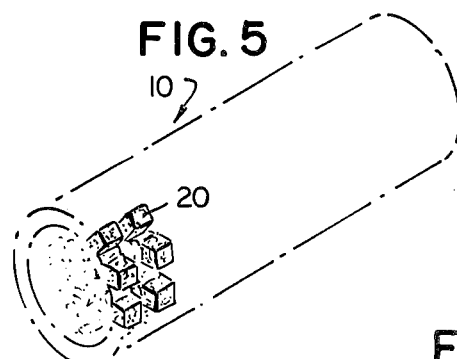
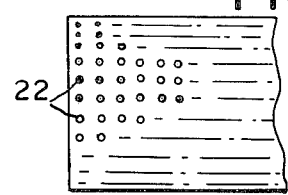
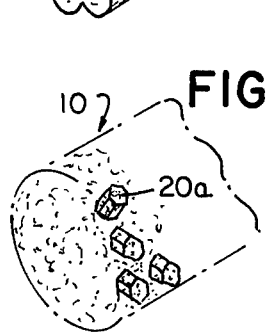
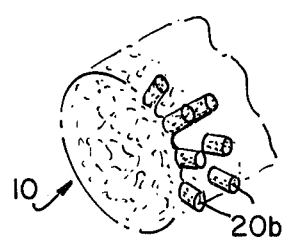
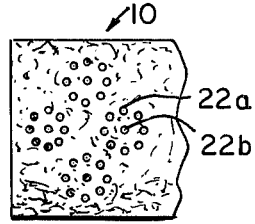
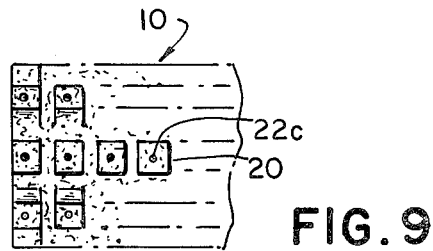

FEMININE HYGIENIC PADS WITH IMPROVED ABSORPTION

BACKGROUND OF THE INVENTION

Urinary exudation is a common female disorder. This is also known as stress incontinence and it involves the discharge of small amounts of urine from the urethral meatus. The female is also subject to other exudations including vaginal and glandular secretions. The resulting wetness and odor are generally disagreeable. This discharge phenomenon may become more pronounced in women having a number of pregnancies or due to other causes such as vaginal infection, venereal disease and so on.

It is the primary object of the invention to provide hygienic pads with improved absorption properties. These pads are made from inexpensive disposable material such as cotton, cellulose, rayon or other synthetic fibers and are adapted to be inserted in the interlabial space between the labia majora.

It is an object of the invention to provide the improved pads with increased surface areas so as to improve the absorption characteristics. The absorbent pads are to be retained in the interlabial space without the need for auxiliary retaining means. This and other objects of the invention are accomplished by providing the pad surface with multiple flutings running in either longitudinal or vertical direction. Alternatively the surface of the pads are provided with absorptive cells of square, round or other configuration.

The flutings and absorptive cells interact with the interlabial membranes providing a suction force to retain the pad in situ without giving the woman any discomfort.

Another object of the invention is to vary the size and/or number of flutings or absorptive cells to vary the absorptive capacity and stiffness of the pad. Thus, one can tailor pads for different conditions of loss of urine and other vaginal exudations, and anatomic requirements.

A further object of the invention is to replace the flutings or absorptive cells by pin holes which also increases the surface area and absorptivity of the pads.

A further object is to provide interlabial pads of pressed cellulose material with improved absorptive capacity but with less tendency to fray and shred.

A further object is to provide various methods of making the pads.

It is to be understood that the pads of the instant invention are not catamenial devices intended to receive bloody menstrual discharge. Nor are the pads of the invention intended for vaginal insertions such as tampons.

Other objects of the invention will be obvious and in part hereinafter pointed out.

DESCRIPTION OF THE DRAWINGS

FIG. 1 shows diagrammatically in cross section the feminine anatomy in the urethral and adjacent areas and shows a pad of the invention being inserted in the interlabial space;

FIG. 2 shows a perspective view of a pad of the invention with longitudinal flutings.

FIG. 3 shows a perspective view of a pad of the invention with vertical flutings.

FIG. 4 shows a perspective view of a pad of the invention with multiple flutings.

FIG. 5 shows a perspective view of a pad of the invention with square absorptive cells.

FIGS. 6 and 6A show in outline hexagonal and round absorptive cells.

FIG. 7 is a perspective view of a pad of the invention which has been provided with pin-cushioning.

FIG. 8 shows a similar view of a pad of the invention in which the pin-cushioning has been arranged in monogram or patterned form.

FIG. 9 shows a pad of the invention in which absorptive cells have been pin-cushioned to give greater absorption.

DESCRIPTION OF THE PREFERRED EMBODIMENTS

Figure 10:
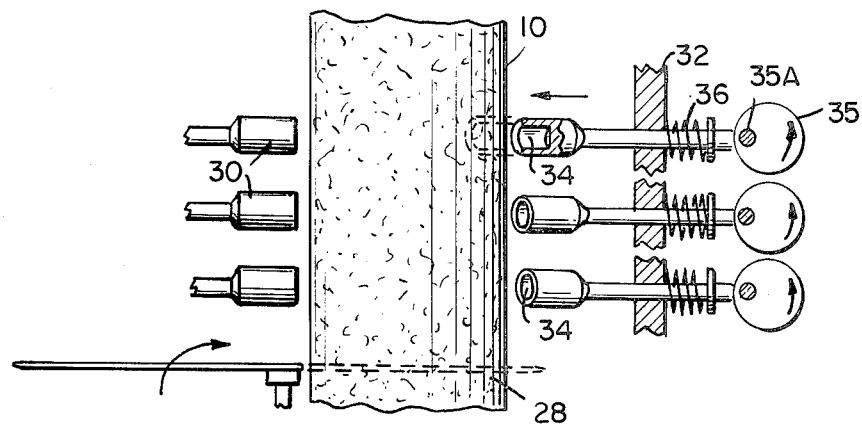
FIG. 10 shows the method by which multiple flutings are pressed into the pad.

Referring to FIG. 1, the reference numeral 11 indicates the urethra extending from bladder 12. The uterus is indicated at 13, the vagina at 14, the rectal colon at 15 and the labia majora at 16.

The pad 10 of the invention is inserted in the interlabial space formed between the lips of the labia majora, thus, covering the urethral meatus which is the external orifice of the urethra 11 from which the urine is ejected and the orifice of the vagina 14.

Other exudations may originate from various glands and organs located in this area of the female anatomy and tend to leak out through the interlabial space.

The pad 10 of the invention is approximately 2 inches in length, measured horizontally, having reference to the position of the pad in the erect female as shown in FIG. 1. In diameter the preferred pad of the invention may be about $\frac{5}{8}$" thick and this is the extent to which the pad of the invention extends into the interlabial zone.

The terms "vertical" and "horizontal" as used herein for convenience refer to the position of the body shown in FIG. 1. The term "longitudinal" refers to the longer axis of the pad. Thus, in the embodiment shown in FIG. 2 the pad 10 is formed with a multiplicity of longitudinal flutings 16. The crests 16a of the flutings lie on a circle or ellipse having a $\frac{5}{8}$" diameter. The valleys or depressions 16b of the flutings are located on a circle $\frac{3}{8}$ of an inch diameter. It will be understood that these dimensions are approximate only and are not in any way limitive. They are given by way of example to give some idea of the size of the pad of the invention.

In the embodiment of FIG. 3 the flutings 18 extend circumferentially or vertically having regard to the direction in which the pad 10 is inserted.

In the FIG. 4 embodiment the pad 10 is fluted both in the horizontal and vertical directions resulting in a pad surface with a large number of humps or protuberances 19 somewhat resembling the surface of a pineapple.

It will be understood that the pad 10 is made of cotton, cellulosic or synthetic fibers pressed into a generally cylindrical basic shape with the major axis of the cylinder extending transversely to the direction of insertion. As shown later with reference to FIGS. 16, 16A, 16B and 16C, the basic shape of the pad may also be of rectangular, hexagonal or elliptical cross-section.

The overall geometry of the cross-section of the final pads can be any of the above shapes. The longitudinal aspect of the pad can be of uniform cross-section or tapered at one or both ends.

Instead of flutings, the surface area of the pad 10 can be increased by the provision of absorptive cells 20 protruding outwardly from the cylindrical or other basic shape of the pad body. The absorptive cells may be square as shown in FIG. 5. The cells 20a and 20b may also be polygonal or hexagonal as shown in FIG. 6 or round as shown in FIG. 6A.

Instead of using absorptive cells protruding from the body of the pad, the absorptive capacity may be increased by putting pin-like holes 22 into the surface. This embodiment, generally, referred to as pin-cushioning is illustrated in FIG. 7. The holes 22 may be about 1/16 of an inch in diameter and take up one fourth of the thickness of the pad.

The pin holes 22 may be arranged in patterns or in the form of monograms as shown in FIG. 8 with a large number of smaller holes 22a surrounding a few larger holes 22b.

FIG. 9 shows an embodiment in which the absorptive cells 20 of the pad 10 shown in FIG. 5 are pin-cushioned at 22c for greater absorption.

It has been noted that pin-cushioning of pressed fiber pads prevents fraying and shredding of the pad surfaces besides increasing absorption. Pressed fiber pads with flutings and absorptive cells also have less tendency to fray and shred.

Varying the size and/or number of flutings or absorptive cells varies the absorptive capacity and stiffness of the pad. Thus, one can tailor pads for different conditions of loss of urine and vaginal exudations and anatomical requirements. Likewise varying the number, size and depth of pin-cushions varies the absorptive capacity and stiffness of the pad as above.

Various preferred methods of providing the pads of the invention with flutings, absorptive cells and pin-cushioning will now be described in greater detail.

Referring first to FIG. 10, the basic cyclindrical pad 10 during the manufacturing steps is in the form of a long cylindrical strand 28 (a short portion only being shown). The strand is run in a generally vertical direction through a fluting device using pressure technique. In the embodiment shown this device consists of a plurality of pressure fingers 30 which are circumferentially disposed in relation to strand 28. FIG. 10 shows six of these fingers located in the plane of the material. In the actual embodiment a great number of these fingers 30 are equidistantly spaced circumferentially around the longitudinal axis of the strand 28 (which is here vertically disposed). The fingers 30 are mounted in vertical guide walls 32 and are adapted to be oscillated in their horizontal plane radially toward the strand. The finger tips are thus made to impinge upon the surface of the strand and penetrate the matted fibrous surface of the strand to an extent of about ⅛ of an inch creating a surface with multiple flutings. In this way the fibers in the area contacted are caused to be compressed and the strand can be impacted with any desired pattern.

Figure 11:
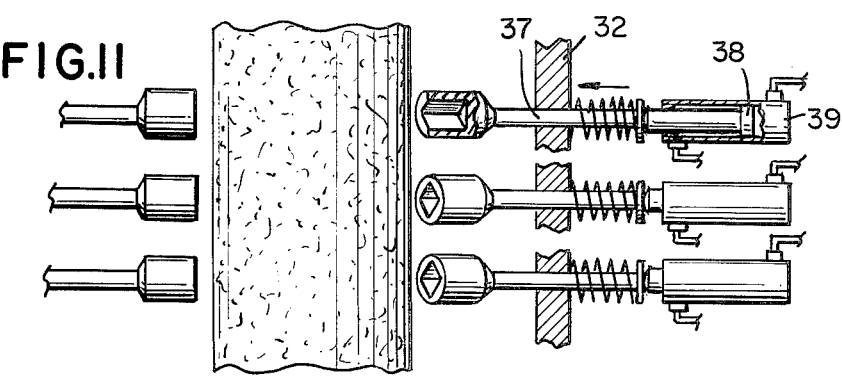
FIG. 11 shows the method by which molds press the material of the pad to create absorptive cells.

The tips of the fingers can be of generally round or square configuration as shown in FIGS. 10 or 11. Unlike the flutings, round absorbtive cells are about 1/16 of an inch deep. The finished pad will then have its surface studded with a plurality of absorptive cells 20 similar to those shown in FIGS. 6A or 5. The finger tips, alternatively, can be hexagonal in shape corresponding to the embodiment already referred to in connection with FIG. 6.

In the form of the invention shown in FIG. 10 the tips 34 of the fingers are annular-faced with hollows in the interior of the annuli to accommodate those fibers which are not to be subject to compression. The inner diameter of the annuli thus will correspond to the width of the absorptive cells formed on the finished pad which will have the appearance not unlike that of a hand grenade.

Figure 12:
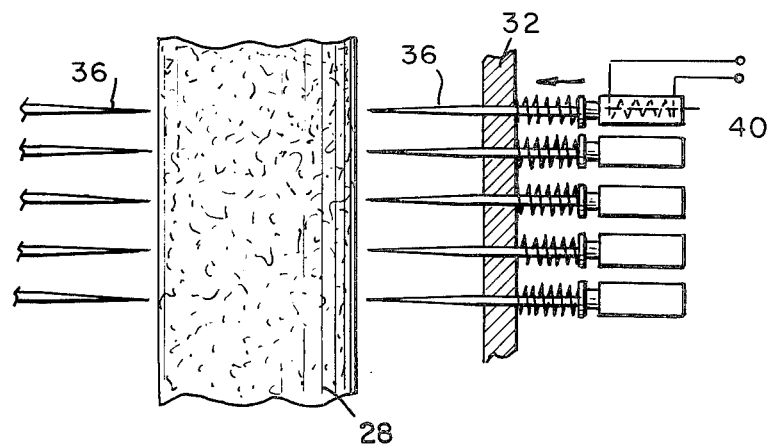
FIG. 12 shows the method by which the pads of the invention are formed with pin holes to create pin-cushioning.

The pin-cushioning of the pads which has already been described with reference to FIGS. 7 and 8 can be simply accomplished by arranging a large number of radial pins 36, as shown in FIG. 12. The oscillatory movement of the pins towards the vertically travelling strand of pressed cotton 28, cellulose or the like can again be accomplished either mechanically, pneumatically or electrically.

The oscillatory movement of the fingers can be effected mechanically by a cam action shown in FIG. 10. In this form the cams 35 would be mounted on horizontal spindles 35A disposed behind walls 32 and as the spindles rotate the cams would thrust the fingers towards strand 28. At the moment of impact the vertical movement of the strand is momentarily arrested so that the compacting action can be completed. As the cams continue to rotate the fingers are withdrawn into walls 32 for instance by means of helical springs 36 which were compressed by the previous radial inward movement of the fingers.

In an alternative form shown in FIG. 11, instead of the cams, the radial inward movement of the fingers can be accomplished by pneumatic means. In this form each finger is mounted on a stem 37 carrying a little piston 38 moving in a cylinder 39. Thus, by forcing air under pressure into each of these cylinders the fingers can be moved inwardly to form the compacting action on the strand.

In a third electrical form shown in FIG. 12 each finger stem could be surrounded by a solenoid 40. As the solenoid is excited the stem would then be moved radially by magnetic action.

Other means or methods of operating the radial pins will occur to those familiar with the operation of knitting machines.

It will be understood that the strand after having passed the areas of impaction shown in FIGS. 10, 11 and 12, will be cut into small segments corresponding in lengths to the finished pads. If the strand travels vertically in a downward direction, this can be readily accomplished by arranging radial knives (not shown) at a convenient distance below the radial fingers. The pad segments are then cut off, the knives being timed to move inwardly in synchronism with the fingers immediately above. The vertical movement of the strand is arrested during this radial inward movement, has already been explained, and in this way it will be possible to effect a clean cutting action.

The ends of the pads may be tapered or rounded off and this can be accomplished by coupling the cutting action with a further compressing action or using curved knives.

To create the monogram design shown in FIG. 8 it would be necessary to cluster the pins and adjust their relative spacing so as to accomplish the desired pattern.

As has already been described in relation to FIG. 9, the surface area of the absorptive cells can be further increased by pin-cushioning. To accomplish this a pin-cushioning device of the type shown in the outline in FIG. 12 may be located vertically below the mold arrangement shown in FIG. 10 for the formation of the absorptive cells or the pins can be placed in the hollow of the absorptive cell or fluting mold.

Another method of making flutings in the absorptive pads is to sew the pad with yarn-like material to give a shaggy surface to the pad.

Figure 13:
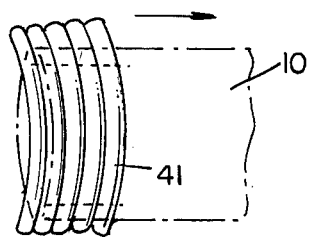
FIGS. 13, 13A and 14 show various methods of sewing on yarn-like material to impart to the pad a fluted surface.
Figure 13A:
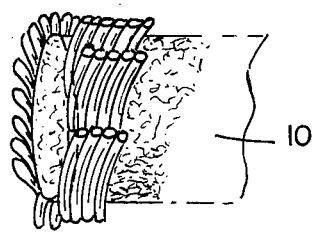

In FIG. 13 a method is shown of sewing yarn-like material to the pads. The pad 10 is shown in broken line. Short pieces of yarn 41 are stitched to the cylindrical surface of the pad by automatic sewing machine heads arranged diametrically on either side of the fibrous strand which in this form of the invention is travelling in a horizontal direction as shown by the direction of the arrow. Two or three stitching heads are arranged equidistantly around the diameter of the strand so as to equalize radial pressure as the strand is travelling from left to right. In this form of the invention, movement of the strand could be continuous. The appearance of the finished pad, which is cut off in segments after the stitching operation, is shown in FIG. 13A.

Figure 14:
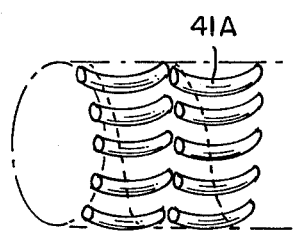

Short pieces of yarn-like material 41A to be stitched on by the method illustrated in FIG. 13 may be oriented lengthwise in the direction of travel of the strand, see FIG. 14. Alternatively, a spiral stitch may be adapted with the stitching head or heads moving helically around the vertically travelling strand. Such stitching methods could be similar to the knitting of hose.

A third method may be to fold or roll up shaggy material and then cut off suitable segments.

Figure 15:
FIGS. 15, 15A and 15B show a modified method of using shaggy material and folding them into a pad.
Figure 15A:
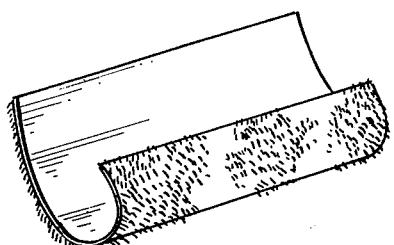
Figure 15B:
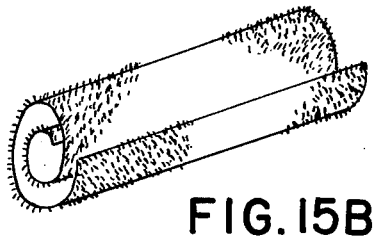

Instead of stitching short pieces of yarn to a cylindrical base, one can start with a planar shaggy material (FIG. 15) similar to the type used for carpeting and fold this into tubular form as in FIGS. 15A and 15B and then apply transverse stitching to maintain the shape of the tube as in FIG. 15B.

Figure 16:
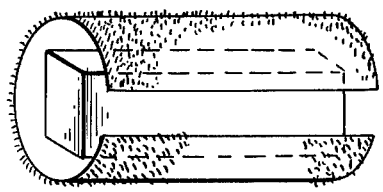
FIGS. 16, 16A, 16B and 16C show a method of folding or wrapping shaggy material around a base or mold of rectangular, hexagonal, cylindrical or elliptical cross-section.
Figure 16A:
Figure 16B:
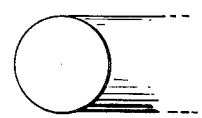
Figure 16C:
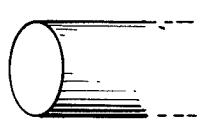

In yet another method of the invention, the shaggy material is wrapped around a base or mold, which may be rectangular, polygonal e.g. hexagonal or cylindrical in cross-section as shown in FIGS. 16, 16A or 16B.

What is claimed is:

1. A feminine hygienic pad with improved surface sorption properties for use in the interlabial space in the area of the female urethral meatus and vaginal meatus for sorption of urine and other undesirable exudations comprising an elongated fibrous pad base of rod-like configuration having a continuous exposed exterior surface thereabout, the pad base including exposed integral surface protuberances of sorptive cells, said protuberances projecting perpendicularly outward from the exterior surface of said pad at equally spaced points spaced longitudinally and peripherally about substantially the entire exterior surface thereof; said protuberances comprising parallel side walls, said protuberances adding multiple sorptive surfaces to the exposed exterior surface of the pad base and increasing the effective exposed exterior sorptive surface area of the pad, and holes formed in at least selected ones of said protuberances and opening outward through said exterior surface to expose additional sorptive surfaces.

2. The feminine hygienic pad as in claim 1 wherein said protuberances have a square cross section when the sectional plane is perpendicular to the axis of symmetry of said protuberances.

3. The feminine hygienic pad as in claim 1 wherein said protuberances have a hexagonal cross section when the sectional plane is perpendicular to the axis of symmetry of said protuberances.

4. A feminine hygienic pad as in claim 1 wherein the cross section of said protuberances is circular when the sectional plane is perpendicular to the axis of symmetry of said protuberances.

5. A feminine hygienic pad as in claim 1 wherein said protuberances have a generally arcuate outer end exterior surface.

* * * * *